(12) United States Patent
Stegmann

(10) Patent No.: US 12,721,749 B2
(45) Date of Patent: Sep. 1, 2026

(54) APPARATUS FOR THERMAL THERAPY TREATMENT OF A SELECTED REGION OF THE BODY OF A HUMAN OR OF AN ANIMAL AND METHOD OF OPERATING SAID APPARATUS

(71) Applicant: HILOTHERM HOLDING AG, Oberwil bei Zug (CH)

(72) Inventor: Christian Stegmann, Burgberg im Allgäu (DE)

(73) Assignee: HILOTHERM HOLDING AG, Oberwil bei Zug (CH)

( * ) Notice: Subject to any disclaimer, the term of this patent is extended or adjusted under 35 U.S.C. 154(b) by 0 days.

(21) Appl. No.: 19/287,403

(22) Filed: Jul. 31, 2025

(65) Prior Publication Data

US 2025/0360023 A1 Nov. 27, 2025

Related U.S. Application Data

(63) Continuation-in-part of application No. 18/252,332, filed as application No. PCT/EP2021/081335 on Nov.

(Continued)

(30) Foreign Application Priority Data

Nov. 11, 2020 (EP) .................................... 20206941

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/0018* (2013.01);

(Continued)

(58) Field of Classification Search
CPC ...... A61F 2007/0018; A61F 2007/0036; A61F 2007/0045; A61F 2007/0054;

(Continued)

(56) References Cited

U.S. PATENT DOCUMENTS

2012/0172774 A1 7/2012 Lowe et al.
2013/0296981 A1 11/2013 Saggers (Continued)

FOREIGN PATENT DOCUMENTS

DE 102015003473 A1 9/2015
DE 102014012638 A1 2/2016

(Continued)

OTHER PUBLICATIONS

"10-12 ° C., Hilotherapie, zur Vermeidung der Polyneuropathie (CIPN) and des Hand-Full-Syndroms (HFS)", Hilotherm GmbH, 5 pages.

(Continued)

*Primary Examiner* — Tigist S Demie
(74) *Attorney, Agent, or Firm* — Kilpatrick Townsend & Stockton LLP

(57) ABSTRACT

The invention relates to a device and method for thermal therapy of a selected region of a human or animal body, particularly for treating tissue damage after surgery, injuries, inflammation, chronic rheumatic conditions, and for supporting chemotherapy. The system includes a temperature control device that circulates a temperature-controlled fluid through a heat transfer unit configured for uniform skin contact, and a pressure device to optimize thermal transfer. During chemotherapy, the device maintains the selected region, such as hands or feet, at a target temperature to prevent or reduce chemotherapy-induced polyneuropathy (CIPN). Sensors monitor temperature and pressure, enabling feedback control for consistent therapy. Methods include (Continued)

fitting the device to the patient, adjusting pressure, and maintaining even skin cooling throughout chemotherapy, thereby improving patient comfort, reducing adverse side effects, and supporting adherence to treatment. The invention provides improved outcomes in thermal therapy applications.

16 Claims, 3 Drawing Sheets

Related U.S. Application Data

11, 2021, which is a continuation of application No. 17/365,957, filed on Jul. 1, 2021, now Pat. No. 12,409,061.

(52) U.S. Cl.
CPC ................ *A61F 2007/0055* (2013.01); *A61F 2007/0217* (2013.01); *A61F 2007/0252* (2013.01); *A61F 2007/0287* (2013.01)

(58) Field of Classification Search
CPC ...... A61F 2007/0055; A61F 2007/0056; A61F 2007/0076; A61F 2007/0086; A61F 2007/0091; A61F 2007/0092; A61F 2007/0217; A61F 2007/0225; A61F 2007/0252; A61F 2007/0268; A61F 2007/0273; A61F 2007/0274; A61F 2007/0287; A61F 7/007; A61F 7/0085; A61F 7/02
See application file for complete search history.

(56) References Cited

U.S. PATENT DOCUMENTS

2015/0328042 A1 11/2015 Parish et al.
2015/0351957 A1* 12/2015 Wilder-Smith ........ A61B 5/026 607/104
2016/0338873 A1 11/2016 Parish et al.
2019/0133817 A1 5/2019 Hilton et al.
2020/0375793 A1* 12/2020 Dilligan ................ A61F 7/0085

FOREIGN PATENT DOCUMENTS

DE 102017200034 A1 7/2018
DE 202018107423 U1 3/2020
EP 1972312 A2 9/2008
EP 2194940 A1 9/2011
EP 2462906 A1 6/2012
EP 2999441 A2 3/2016
WO 2014/188213 A2 11/2014
WO 2016/016610 A1 2/2016

OTHER PUBLICATIONS

U.S. Appl. No. 17/365,957, Advisory Action, mailed Jul. 1, 2025, 3 pages.
U.S. Appl. No. 17/365,957, Final Office Action, mailed Jan. 16, 2025, 20 pages.
Schaper, "Polyneuropathie, Pilotprojekt belegt: Neuartige Hilotherapie, Vermeidet Schmerzhafte Nervenerkrankung", Available online at: https://hiloterapia.net/wp-content/uploads/Hilotherapie.pdf, 2018, 1 page.
Schaper, "The Prophylactic Use of Hilotherapy® (Physical Thermotherapy) Prevents Chemotherapy Induced Peripheral Neuropathy (CIPN)", European Breast Cancer Institute, Available online at: https://www.hilotherm.com/wp-content/uploads/2020/07/2019-Chemo-Engl.pdf, Sep. 2019, 27 pages.
Schaper, "Vermeidung der Chemotherapie-induzierten Polyneuropathie (CIPN)", Available online at: https://www.hilotherm.com/wp-content/uploads/2020/07/2020-Studie-Chemotherapie-Maerz-2020.pdf, 2020, 33 pages.
Schubert, "Hilotherapy the Thermal Procedure, Controllable to the Nearest Degree", Hilotherm GmbH, 2016, 4 pages.
International Search Report and Written Opinion of the ISA for PCT/EP2021/081335, mailed Apr. 7, 2022, 22 pages.
Extended European Search Report issued in EP Application No. 20206941.5, mailed Apr. 19, 2021, 12 pages, including English translation.

* cited by examiner

APPARATUS FOR THERMAL THERAPY TREATMENT OF A SELECTED REGION OF THE BODY OF A HUMAN OR OF AN ANIMAL AND METHOD OF OPERATING SAID APPARATUS

This application is a continuation in part application and claims the benefit of copending U.S. patent application Ser. No. 18/252,332, filed May 9, 2023, which is a 371 National phase filing of PCT/EP2021/081335 filed Nov. 11, 2021, which is a continuation of copending U.S. patent application Ser. No. 17/365,957, filed Jul. 1, 2021, which claims priority to European Patent Application No. 20206941.5 filed Nov. 11, 2020. The entire contents of each of these application are hereby incorporated by reference.

The present invention relates to a device for use in the thermal therapy treatment of a selected region of the body of a human or of an animal, and in particular for use in the treatment of tissue damage after surgical interventions, of injuries, of inflammations and of chronic diseases of the rheumatic type, and in particular for assisting chemotherapeutic treatments, as well as a method of operating such a device.

In the context of the present invention, the term "thermal therapy treatment" is intended to be understood to mean a treatment in which heat is supplied to the human or animal body, or removed therefrom.

Preferably, this is not a matter of supplying heat to, or removing heat from, the entire body, as is done, for example, in a sauna and the subsequent immersion in a plunge pool filled with cold water, but it is preferably a matter of supplying heat to, or removing heat from, a selected region of the human body, for example the limbs, regions of the back, the abdomen, the chest or the head, in order to achieve therapeutic effects.

Known devices for thermal therapy treatment have temperature control devices which are as described, for example, in European patents EP 2 194 940 B1 and EP 2 462 906 B1. These temperature control devices comprise a cooling unit and/or a heating unit by means of which a fluid, preferably water, is cooled and/or heated to the desired temperature. Preferably, one or more pumps are also provided, by means of which the temperature-controlled fluid is conveyed, via connecting hoses, to a heat transfer device.

DE 20 2018 107 423 U1 shows an example of a heat transfer device by means of which the heat generated by the temperature control device is transferred to the selected region of the body. The device shown there, which, in this document, as well as in practice is usually referred to as a cuff, comprises a first and a second flexible material layer between which flow spaces are provided through which the tempered fluid flows. These cuffs can be constructed in many different shapes for a predetermined region of the body, for example as a hand cuff, forearm cuff, knee cuff, calf cuff, round cuff, chest cuff or face cuff. Further, they can be constructed as trapezoidal cuffs or surface cuffs, which, depending on their size and shape, are suitable for being placed on any desired region of the body. Fasteners, tapes and the like are used to secure the cuffs to the body.

Although the devices mentioned above have proven themselves in practice, there is a desire for further improvement. It is therefore an object of the present invention to improve the device already known.

Thermal therapeutic measures also have a particular significance in the treatment of cancer by means of chemotherapy. The chemotherapeutic agent which is used to reduce cancer cells penetrates into the blood capillaries of the hands and feet and can lead to the feared chemotherapy-induced polyneuropathy (CIPN) or hand-foot syndrome (HFS) with permanent damage to the tissue and in particular the nerve cells.

This problem is solved, at least in some embodiments, by the methods of claim 1 and claim 7.

Chemotherapy-induced peripheral neuropathy (CIPN) and hand-foot syndrome (HFS) are common and debilitating side effects of several chemotherapy agents, particularly taxanes and platinum-based drugs. These conditions can cause pain, numbness, tingling, and functional limitations in the hands and feet, severely impacting a patient's quality of life. Importantly, the severity of these symptoms often forces oncologists to reduce chemotherapy doses or discontinue treatment prematurely. Such modifications can compromise the effectiveness of cancer therapy, leading to suboptimal outcomes, including lower survival rates and increased risk of disease recurrence. Preventing or mitigating CIPN and HFS is therefore essential to maintaining treatment intensity and achieving the best possible prognosis for patients.

This problem is solved, in at least in part, by the method of claim 12.

The disclosure of the documents EP 2 194 940 B17-07-27, EP 2 462 906 B17-07-27, DE 20 2018 107 423 U1 mentioned above, as well as DE 10 2015 003 473 A1 are hereby incorporated by reference in the disclosure of the present invention.

The device in accordance with the invention has a temperature control device which is provided in order to control a temperature of a temperature control fluid. For this purpose, the temperature control device is connected, in a fluid conducting manner, to a heat transfer device, which is arranged to transfer heat to the selected region of the body, and is further arranged to temper the heat transfer device with a heat transferring temperature control fluid flowing through the heat transfer device. The device further comprises a control device which is connected to the temperature control device and to the heat transfer device, whereby the control device is arranged to control the temperature control device in order to cause the heat transfer device to be at least partially at an approximately uniform temperature in the region of a contact surface between the heat transfer device and the selected region of the body to be temperature controlled.

The term "control device" is intended to be understood to mean a device which either controls, and/or controls with feedback, parts of the device on the basis of data or values supplied to it and/or data or values or settings entered by a user. The influencing is preferably carried out via actuating devices. An actuating device is intended to be understood to mean any electrical or mechanical component which is suitable for influencing a technical system in a directed manner.

In this regard, the selected region of the body of a human may be any region on the surface of the body. In particular, the selected region may concern one of the limbs, such as an arm or a leg, preferably a hand or a foot. Further, the selected region may also concern a region of the chest, a region of the abdomen, a region of the back or a region of the head. In the following, the skin of the patient in the selected region is also referred to as a skin contact region.

A fluid connection, or a connection which is connected in a fluid conducting manner, is intended to be understood to mean a connection that allows the exchange of a liquid or a gaseous fluid from one location to another location. Typical fluid connections are preferably made via a hose or a pipe. The fluid connections are preferably partially or completely thermally insulated in order to keep the loss of heat or loss of cold as low as possible during the conduction of the fluid, in order to ensure, on the one hand, that an energy-saving construction can be achieved, and, on the other hand, to ensure that the target temperature which the heat transfer device is to reach in the region of the skin contact is maintained as accurately as possible.

According to the invention, a heat transferring temperature control fluid is used. The term "a heat transferring temperature control fluid" is intended to be understood to mean a fluid which, in terms of its function, is arranged to transport the heat stored in it, in the form of thermal energy, to a target location. Advantageously, a heat transferring temperature control fluid is therefore a liquid that is suitable for storing or absorbing a large amount of thermal energy. Preferably, water is used as the temperature control fluid, but it is also preferable to use a mixture of water and salt, or a suitable mineral oil or a synthetic oil.

In one embodiment, the temperature control fluid is water-based. Optionally, a disinfectant is included in the water to prevent growth of biofilm (algae and bacteria). A suitable disinfectant is SANOSIL S003 ($H^2O^2$-based disinfectant with 1.5 g/100 g hydrogen peroxide, 0.003 g/100 g silver).

In the context of the invention, the term "connected" can mean "directly connected", such as preferably a cable or a hose, or "indirectly connected", such as preferably via light, infrared, or radio according to the WiFi or Bluetooth standard. In this context, the temperature control device is directly connected to the heat transfer device, i. e. by means of at least one fluid line, while the temperature control device can also be indirectly connected to the control device, i. e. without a line, via radio or the like.

The region where a contact surface of the heat transfer device is located a short distance from the skin surface of the region of the body to be tempered and where it preferably rests directly on the skin surface is designated as the region of a contact surface between the heat transfer device and the region of the body to be tempered.

According to the invention, the heat transfer device is intended to generate an approximately uniform temperature on the selected region of the body to be tempered. In this regard, the term "an approximately uniform temperature" is intended to be understood to mean that all points in this region of the contact surface of the heat transfer device are within an interval of 10° C., preferably 5° C., particularly preferably 3° C., and further particularly preferably 1° C.

In a preferred embodiment, the heat transfer device comprises, for this purpose, at least one heat transfer unit, which is provided to be brought into contact with the selected region of the body. In this context, the heat transfer unit consists of a substantially flexible material in which one or more temperature control fluid chambers are arranged through which the temperature control fluid can flow.

As a rule, the region of the body to be tempered is not flat, but has concave and/or convex regions. In the context of the present invention, it has been found that these features of unevenness can lead to the formation of individual air pockets between the heat transfer unit and the skin surface of the body to be treated, which air pockets thermally insulate the affected local region of the skin portions of the selected region from the heat transfer unit. As a result of this, the tempering of the selected region becomes uneven and the desired effects of the tempering, in particular an increase or a decrease in blood flow, do not occur evenly.

In order to reduce this effect of limited localized thermal insulation, the heat transfer device comprises a substantially flexible material in order to keep the distance between the heat transfer unit and the region to be tempered over the entire three-dimensional surface as small as possible, whereby the flexibility preferably allows it to lie directly over the selected region to be tempered.

In this context, the temperature control fluid chambers are arranged within the heat transfer unit in such a way that, when the temperature control fluid flows through the temperature control fluid chambers, the heat of the temperature control fluid is transferred as uniformly as possible to the region of the body to be tempered.

In a preferred embodiment, in order to transfer the heat as uniformly as possible, the substantially flexible material of the heat transfer unit comprises at least a first flexible material layer having at least a first skin contact surface which faces at least partially towards a selected region of the body of a human or of an animal, and at least a first temperature control fluid contact surface which faces away from the first skin contact surface. In addition, the heat transfer unit comprises at least a second flexible material layer having at least a second temperature control fluid contact surface, which, between itself and the first temperature control fluid contact surface of the first flexible material layer, at least partially delimits the one or more temperature control fluid chambers through which the heat transferring temperature control fluid can flow.

In this context, the heat transfer unit further comprises at least a first connecting line for supplying a heat transferring temperature control fluid to the heat transfer unit, and at least a second connecting line for discharging a heat transferring temperature control fluid from the heat transfer unit. The first and second connecting lines are connected to the temperature control device in order to heat or to cool the temperature control fluid to the desired temperature in a circulating system.

In this context, by using flexible materials, the heat transfer unit has at least a shape, or can assume such a shape, in which it covers and/or at least partially encloses the selected region of the body of a human or of an animal.

In a preferred embodiment, in order to reduce the effect of the localized thermal insulation by air pockets as described above, the heat transfer device further comprises a pressure device in order to generate, or to increase, a contact pressure of the heat transfer unit on the selected region of the body, in order to thereby reduce, at least partially or even substantially completely, the occurrence of thermally insulating air pockets between the heat transfer unit and the region to be tempered. In this context, the pressure device comprises at least a pressure unit and a support device, wherein the pressure unit is prevented, by the support device, from performing a movement in a direction opposite to the skin contact surface of the selected region.

The pressure unit is constructed to subject the heat transfer unit at least partially to a pressure, which is then absorbed as the contact pressure of the heat transfer device by the portion of the body to be treated. For this purpose, the pressure unit comprises at least one pressure chamber with a predetermined or a variable internal pressure.

The use of a pressure chamber which is filled with a fluid has particular advantages. In a pressure chamber which is filled with a fluid, the pressure within the fluid is always the same. This means that the heat transfer unit is pressed onto the skin portions of the selected region with a uniform pressure. As a result of this, the flexible material of the heat transfer unit can adapt particularly well to convex and/or concave regions of the selected region, as a result of which the occurrence of air pockets is avoided, and a particularly good heat transfer is achieved.

In this context, the contact pressure represents that portion of the surface force which is transferred from the pressure unit via the heat transfer unit to the selected region of the body to be tempered.

A support device is provided in order to build up the contact pressure. The term "support device" is intended to be understood to mean any type of device that is suitable for absorbing surface forces that are oriented in a direction against the direction of the contact pressure.

In a preferred embodiment, the at least one pressure unit comprises a chamber which is filled with a pressure fluid, wherein the at least one chamber which is filled with a pressure fluid is bounded by a flexible material. The term "pressure fluid" is intended to be understood to mean a fluid that can be compressible, preferably air or a gas, or incompressible, preferably water, a mixture of water and salt, a mixture of water and oil, or an oil. However, it is also possible to use other fluids as pressure fluid.

In a preferred embodiment, the at least one chamber filled with a pressure fluid is connected to a pressure line. In this context, the pressure fluid in the at least one chamber filled with a pressure fluid can be subjected to pressure, either manually by means of muscle power by a user, and/or by means of a compressor, via the pressure line that is connected to the at least one chamber filled with a pressure fluid. As a result of this, an internal pressure in the at least one pressure chamber filled with a pressure fluid can be varied. As a result of the variable internal pressure, the contact pressure of the heat transfer device on the portion of the body is thus also adjustable. Preferably, a device is provided which is actuated by means of the muscular force of a human.

In this context, the term "compressor" is intended to be understood to mean a machine that serves the purpose of supplying mechanical work to the pressure fluid and thereby increasing the internal pressure. If the fluid is a liquid, the compressor represents a pump.

In one embodiment, the pressure device comprises a release valve for lowering the internal pressure of the pressure unit.

In a further preferred embodiment, the at least one pressure unit is not formed of a pressure chamber filled with a pressure fluid, but is made of an elastic material, and is also arranged between the support device and the heat transfer unit. Here, the elastic material may be a type of foam rubber, a type of rubber, or a combination of these or similar materials. In this context, the elasticity can be constant over the volume of the pressure unit, but, in some embodiments, it is also conceivable that the elasticity of the pressure unit varies over the volume in order to avoid possible pressure peaks, and/or to apply an increased pressure in a targeted manner, preferably over small radii of the portion of the body to be treated.

In an alternative embodiment, the pressure device comprises at least one pressure unit and a support device, wherein the pressure unit is attached to the support device, and the pressure unit is provided so as to at least partially subject the heat transfer unit to a pressure, wherein the pressure unit comprises a body of an elastic material which is adapted to at least partially increase a contact pressure of the heat transfer device on the selected region. Accordingly, the pressure unit does not need to comprise a pressure chamber. Instead, the body of elastic material itself has sufficient elasticity so that, when the body of elastic material is compressed, it can subject the heat transfer unit to a pressure. Again, the elastic material may be a type of foam rubber, a type of rubber, or a combination of these or similar materials.

The compression of the elastic material can be achieved, for example, by the elastic material being compressed between the support device and the portion of the body to be treated. For example, if the portion of the body to be treated is a hand, the heat transfer device may comprise a hand cuff or a glove or similar, in which the hand may be introduced. Assuming for example a generally symmetric construction, in one embodiment, the heat transfer device could be made up of three layers, whereby each layer effectively forms a pouch: an innermost pouch comprising the at least one heat transfer unit, which is located inside an intermediate pouch comprising the at least one pressure unit, which is located inside an outermost pouch comprising the support device (vaguely similar to the layers of an onion). In this example, the different portions of the heat transfer device (in particular the at least one heat transfer unit, the pressure unit and the support device), in particular their thicknesses, may be dimensioned such that, in the initial state of the heat transfer device (i.e. without the hand inserted), there is little or no space in the innermost pouch, i.e. little or no space in which to insert the hand. Preferably, there is also only little or no space between the innermost pouch and the intermediate pouch, and also between the intermediate pouch and the outermost pouch. When the hand is inserted in the innermost pouch, the material of the pressure unit (i.e. the intermediate pouch) is compressed between the support device (i.e. the outermost pouch) and the hand, with the heat transfer unit (i.e. the innermost pouch) being located between the pressure unit and the hand. The compression of the pressure unit in turn generates a pressure on the heat transfer unit, which may ensure good (thermal) contact between the heat transfer unit and the skin of the hand.

The same or a similar effect can be achieved with other configurations of heat transfer devices, for example heat transfer devices in the form of a forearm cuff, boot or the like. Likewise, a corresponding effect can be achieved if the portion of the body to be treated is not intended to be inserted into the heat transfer device, but if, instead, the heat transfer device is intended to be placed (unilaterally) against the skin of the human or animal to be treated. In this case, the heat transfer device may comprise several layers (e.g. three layers, such as an outer support device layer facing away from the skin, an intermediate layer constituting the pressure unit, and an inner heat transfer device layer facing towards the skin), rather than pouches which are placed one inside the other.

In one embodiment, the pressure unit has a volume, wherein (substantially) the entire volume of the pressure unit is made of the elastic material. This contrasts with pressure units which include a significant portion of substantially non-elastic material, which might negatively impact the elastic properties of the pressure unit. Further, this embodiment also contrasts with embodiments (described above) where the pressure unit forms a pressure chamber which can be filled with a pressure fluid.

More explicitly, in one embodiment, the pressure unit is non-inflatable. In this embodiment, the pressure or compression to be built up in the pressure unit could be generated by the pressure unit being compressed between the support device and the portion of the body to be treated, as described above.

Preferably, whether or not the pressure unit is inflatable, the material of the pressure unit is chosen from among a number of materials such that, in normal use (in particular when fixed to, held against, or wrapped around, a portion of the body to be treated, or when a portion of the body to be treated has been introduced into the heat transfer device) the pressure unit is compressed, at least in some areas, by at least 25%, at least 30%, at least 35%, at least 40%, at least 45%, at least 50%, at least 55%, or at least 60% of its thickness.

In a preferred embodiment, the support device of the pressure device is made of a material which has low flexibility.

In this context, the term "a material which has low flexibility" is intended to be understood to mean a material with a higher modulus of elasticity, such as preferably hard plastic. Above all, it is important here that the material which is used for the support device has a higher stiffness than the pressure unit, in order to conduct the internal pressure of the pressure unit to the contact surface between the heat transfer unit and the selected region of the body and the heat transfer unit.

In one embodiment, the support device may comprise, or be made of, plastics material, for example a sheet of plastics material. The plastics material may, for example, have a thickness selected from at least 0.5 mm, at least 0.8 mm, at least 1 mm, at least 1.3 mm, at least 1.5 mm and at least 1.7 mm. In addition, or as an alternative, the plastics material may, for example, have a thickness selected from at most 2.5 mm, at most 2.2 mm, at most 2 mm, at most 1.8 mm, at most 1.5 mm and at most 1.2 mm. The plastics material may, for example, have a thickness of about 1 mm, 1.3 mm or 2 mm.

In one embodiment, the support device is made of, or comprises, a material having a modulus of elasticity of at least $2\times10^9$ $Nm^{-2}$. By way of contrast, the pressure unit may be made of, or may comprise, a material having a modulus of elasticity of $0.5\times10^9$ $Nm^{-2}$ or less, preferably $0.2\times10^9$ $Nm^{-2}$ or less, preferably $0.1\times10^9$ $Nm^{-2}$ or less.

In one embodiment, the flexibility of a material of the pressure unit is significantly greater than the flexibility of the support device, in particular greater at least by a factor selected from the group consisting of 2, 3, 4, 5, 10, 20, 50 and 100. In one embodiment, this degree of flexibility can be expressed via the modulus of elasticity of the material in question.

In a preferred embodiment, the support device of the pressure device around the selected region of the body of a human or of an animal further comprises a connecting device with at least one fixing element. In this context, the connecting device is constructed in such a way that it at least partially reaches around the pressure device and, in this "reaching around" position, exerts supporting forces onto the pressure device, which at least partially contribute to fixing the pressure device in a "deployed for use" condition to the selected region of the body of a human or of an animal. In this context, the connecting device having at least one fixing element may be continuously adjustable, such as preferably by means of a strap, or may include dedicated attachment points, such as preferably press studs, or may consist of a combination of both.

The term "deployed for use' condition" is intended to be understood to mean a condition in which the heat transfer device is applied to the selected region of the body.

In a preferred embodiment, at least one sensor device is further provided, which is connected to the control device. The sensor device is preferably arranged to measure a sensor signal at specific positions of the device. Preferably, the sensor device is used to measure the temperature and/or the contact pressure between the selected region of the body and the skin contact surface and/or in the heat transfer device and/or in an edge region of the heat transfer device which faces towards the body.

The term "sensor device" is intended to be understood to mean any device that has a sensor for measuring a physical state and which is set up to convert this state into a sensor signal. Here, the sensor signal can be optical, acoustic or digital.

In a preferred embodiment, the at least one sensor device is a plurality of sensor devices, which are preferably at least partially arranged in a grid, preferably in the edge region, or on the surface of the first material layer which, in the "deployed for use" position, faces towards the skin. In this context, the grid may be a grid with identical distances, or a grid with almost identical distances, or a grid with different distances, or a combination thereof.

Here, in a preferred embodiment, the measured sensor signal is selected from the group of pressure, electric current and temperature. However, other physical variables are also conceivable.

In a preferred embodiment, at least one display device is provided. The display device is connected to the control device and is set up to output the sensor signal measured by the sensor device to a user via the display device.

In this context, the display device can comprise any form of display facility that enables information to be provided to a user about the status of the individual devices and/or the measured sensor signal. Thus, the display can be visual, preferably in the form of a screen, acoustic, preferably in the form of an audible sound, but also haptic, preferably in the form of a vibration. However, other forms of display are also conceivable.

A temperature control device is provided in order to supply to, or remove from, the heat transferring fluid, the energy necessary for the temperature control of the selected region of the body. The temperature control device preferably has a housing, preferably a temperature control fluid supply device by means of which a heat transferring temperature control fluid is provided in the housing, and at least one temperature control unit, which is preferably arranged in the housing and by means of which the heat transferring temperature control fluid is temperature controlled. Further, the temperature control device has at least one temperature control fluid outflow device, through which the heat transferring temperature control fluid is led out of the housing at a substantially predetermined temperature, and preferably at least one pumping device, which is preferably arranged in the housing and which applies pressure to the heat transferring temperature control fluid flowing through the housing.

The temperature control unit preferably comprises an electric heating unit. Further preferably, the temperature control unit comprises at least one conventional cooling unit in which a refrigerant is compressed, expanded via a thermal expansion valve and condensed via a condenser.

Particularly preferably, the temperature control unit has, in addition or exclusively, at least one temperature control element which is constructed as a thermoelectric element, in particular as a Peltier element. Preferably, a heat exchange element through which a temperature control fluid can flow is also provided, in order to transfer heat to, or from, the temperature control fluid, and preferably at least one cooling unit.

Preferably, the device uses at least one of the three groups of sensors described in the following.

A first group of sensors is provided to detect the condition of the heat transfer device and, if applicable, the connecting lines as well.

This includes temperature sensors that sense the temperature at predetermined locations of the heat transfer device and the connecting lines, pressure sensors that measure the pressure forces of the pressure unit within the heat transfer device, and sensors for flow measurement by means of which the flow rate and/or the amount of temperature control fluid which is being supplied and/or discharged can be detected.

A second group of sensors is provided within the temperature control unit. Here, too, temperatures, pressure and flow velocity or flow volume are preferably detected.

A third group of sensors is provided for taking measurements of physiological data on the patient, which are preferably used by the control device to control, and/or control with feedback, the operation of the device and in particular the temperature of the heat transfer device.

Preferably, temperature sensors are used, which are preferably arranged in the form of thin electrodes in the selected region of the body to be tempered by the device. Furthermore, pressure sensors are preferably used, also preferably in the form of thin electrodes, by means of which the contact pressure of the heat transfer device can be detected.

Further preferably, sensors are used which detect the physiological state of the patient being treated. For this purpose, one or more sensors are selected from a subgroup which comprises the sensors mentioned in the following: sensors that measure the heart rate, sensors that record an ECG, sensors that measure the blood pressure, and preferably sensors that measure the blood flow.

In a preferred embodiment, the control device is set up to form one or more control loops on the basis of the signal(s) measured by the sensor devices or sensors, in such a way that a region of a contact surface between the heat transfer device and the portion of the body to be tempered has, at least in one region, an approximately uniform, preselected temperature.

The device preferably has one or more actuating or feedback control devices that allow parameters of the device such as the temperature of the fluid, the flow rate, the amount of fluid delivered, and the like to be changed. These actuating or feedback control devices may be electrical feedback control devices that preferably have an influence on a voltage, a frequency and/or a current. Further preferably, the feedback control devices may be mechanical feedback control devices that can preferably change the flow resistance and/or stop the flow, or they can be electromechanical in construction.

The control device is equipped with at least one, preferably however with two, or further preferably with a plurality of operating elements which enable the desired treatment parameters to be set. Preferably, this includes the specification of operating times and stand down times, as well as the specification of temperatures or temperature intervals.

Depending on the area of application, when the device is used for cooling, the following temperature ranges are particularly advantageous and should be covered by the respective device. For use in hospitals etc., a temperature range of 10-35° C. is recommended, for hospital and outpatient treatments a temperature range of 12-22° C., and for treatment in a private setting a temperature range of 15-22° C. However, it is also preferred to construct the device in such a way that it covers a wider temperature range of 10-35° C., or even a temperature range of 10-43° C.

Preferably, the control device comprises a processor device and a memory device. One or more program routines are preferably stored in the memory device, which, individually or together, are used to influence or to control, by means of the processor device, the operation of the control device and preferably also parts of the device. The program routines are preferably predetermined and permanently stored in the memory device. Further preferably, the program routines can be modified by the user and/or additional program routines can be entered into the memory device.

In particular, but not exclusively, in the case of a device that is used only, or also, in a private setting outside a hospital or other medical facility, part or all of the control of the control device may be performed by an external processor device. Preferably, a stationary or transportable computer, such as preferably a laptop computer, is used for this purpose. Further preferably, a mobile communication device, in particular a cell phone or particularly preferably a smartphone, is used as the external processor device. Preferably, the mobile communication device, in particular a smartphone, is connected to external sensors that can detect physiological data of the patient. Preferably, sensors that can be attached to the body of the patient are used for this purpose, such as for example wristbands with sensors, or a smartwatch. The programs used on the mobile communication device for collecting physiological data, such as preferably the heart rate and ECG functions, can then be used to control the device.

Preferably, the device features an alarm mode. This alarm mode is preferably triggered when a temperature is not within a desirable range. Preferably, this may be the case when the fluid temperature rises above a predetermined value or when, further preferably, a housing temperature assumes a value that is not desired. Further, the alarm mode may also be triggered when the physiological values which the sensors which are connected to the patient detect are within a range that is not desired.

In the examples, mentioned above, in accordance with the invention, there is provided a method of operating a device for carrying out thermal therapy treatment of a selected region of the body of a human or of an animal, wherein the method comprises the following steps. At the start, a heat transfer device is brought into a "deployed for use" condition in contact, by means of a pressure device, with the selected region of the body. A contact pressure acting on the selected region of the body is then applied via the pressure device. The selected region of the body is tempered via a temperature control device connected to the heat transfer device, in that a heat transferring temperature control fluid flows through a heat transfer unit of the heat transfer device, so that in the region of a contact surface between the heat transfer device and the portion of the body to be tempered has an approximately uniform temperature in at least one region.

The term "bringing the heat transfer device into contact" can preferably be understood to mean the placing of a cuff containing a heat transfer device around a hand of a patient. Further, the term "bringing into contact" can also be understood to mean the placing of a body part on a heat transfer device resting on a cushion.

In a preferred embodiment, the method further comprises the following step:

An internal pressure of a pressure unit of the pressure device is set, wherein the pressure unit comprises at least one chamber which is filled with a pressure fluid. In this context, the internal pressure of the at least one chamber filled with a pressure fluid can be manually adjusted via muscle power of a user and/or via an external pressure source.

In a preferred embodiment, the method further comprises the following steps:

A sensor signal is measured via a sensor device connected to the heat transfer device.

A pressure device which is connected to a control device is then controlled via the control device on the basis of the measured sensor signal. This form of controlling can also be referred to as a control loop.

In the following, therapeutic treatments will be described for which the device in accordance with the invention is particularly suitable:

A targeted heat treatment before a surgical procedure improves the capillary circulation and promotes the healing after the procedure. To this end, heat is applied several times about 18 hours before the operation using the device in accordance with the invention, whereby tempering of the tissue to 41-43° C. is particularly advantageous. This tempering is applied, for example, three times for half an hour each time, interspersed by a cooling phase at room temperature, which also lasts half an hour each time.

For this purpose, a sequence program is stored or entered in the device, which sequence program controls the timing and the various components of the device. It is particularly preferred that physical data (temperature, pressure, etc.) or physiological data is used for this purpose, which is measured by means of the sensors.

After a surgical intervention, but also in particular after injuries and in the case of chronic diseases and any swelling resulting therefrom, internal bleeding, hematomas, edema and inflammation, cooling of the affected tissue with the device in accordance with the invention promotes the healing process and reduces the intensity of pain, which can result in a significantly reduced administration of drugs. This therapeutic effect can be explained by the fact that the affected tissue reacts to the intervention or the injury with inflammation and thus overheating, as a result of which the oxygen demand is increased. Cooling of the tissue reduces this oxygen demand and prevents cell death. To this end, the device is controlled in such a way that a specific target temperature is reached.

For example, the target temperature for achieving the cooling of the tissue may be 14.5° C. Whether the target temperature has been reached can be monitored by the sensors, and additionally the physiological condition of the patient can be monitored, and the control device can be switched off, if necessary, if the values for the heart rate, blood flow or the like are in a range that is not desired.

Thermal therapeutic measures also have a particular significance in the treatment of cancer by means of chemotherapy. The chemotherapeutic agent which is used to reduce cancer cells penetrates into the blood capillaries of the hands and feet and can lead to the feared chemotherapy-induced polyneuropathy (CIPN) or hand-foot syndrome (HFS) with permanent damage to the tissue and in particular the nerve cells. In mild cases, this manifests itself as disagreeable skin sensations, “tingling” and the like; in severe cases it manifests itself as extensive or complete numbness, which can make it difficult to use the hands or even to walk. Furthermore, pain with sometimes high intensity is also reported. In severe cases, onycholysis, i. e. the detachment of one or more nails, also frequently occurs.

According to common understanding, the preferential attack of the sensitive nervous system is due to the blood supply of these nerve cells with fenestrated capillaries. This means that the protein composition of the cell wall is different, i. e. more permeable, to certain chemotherapeutic agents. Thus, they unfold elementary damage to the nerve cells. The damage to the cellular DNA, as well as the mitochondrial DNA, a disturbed calcium balance and oxidative stress promote the dissolution of the ganglion cells. Since the longest nerve fibers are more sensitive to these damaging influences, CIPN usually presents itself as length-dependent, with an emphasis on the lower extremities.

The cooling of the hands and feet or other regions of the body during chemotherapy with the device in accordance with the invention has the effect of reducing the oxygen demand of the cooled tissue and/or reducing the metabolism in the cooled regions and/or reducing blood flow to these regions, as a result of which less therapeutic agent reaches the blood capillaries and the development of polyneuropathy can be prevented. This can also advantageously be achieved with the device in accordance with the invention and with the method of operating the device in accordance with the invention.

The cooling of the hands and feet or other regions of the body during chemotherapy with the device in accordance with the invention also has the effect of reducing the excretion of chemotherapeutic agents from the sweat glands, thereby reducing the likelihood of HFS development.

The cooling is preferably carried out in a temperature range between 8° C. and 30° C., but particularly preferably in a range between 10° C. and 14° C. A cooling temperature in the range of 10° C. to 12° C. is even more preferred.

Preferably, the thermal treatment which has been explained above in relation to surgical procedures is also applied to the treatment in connection with chemotherapy in the form of a cold treatment. To this end, the device in accordance with the invention is preferably used to apply cold about 30 min prior to the administration of the chemotherapeutic agent, whereby tempering of the tissue surface or skin surface of the selected region to 10° C. to 12° C. is particularly advantageous. This tempering is preferably applied during the entire administration of the chemotherapeutic agent, as well as preferably for 1 hr to 3 hr after the completion of the administration of the chemotherapeutic agent.

Preferably, cytostatic drugs such as for example carboplatin, capecitabine, 5-Fu, cyclophosphamide, cytarabine, docetaxel, doxorubicin, oxaliplatin, paclitaxel, sorafinide and sunitinib are used as the chemotherapeutic agents for chemotherapy. These designations are trade names that are protected for the respective manufacturing or distribution companies. The list of these chemotherapeutic agents is not to be understood as a limitation. Embodiments of the present invention can be used in connection with other chemotherapeutic agents, in particular those which can result in CIPN, HFS and other side effects discussed herein, in particular those chemotherapeutic agents which can result in side effects which can be reduced or even eliminated through cooling of the hands and/or feet and/or other body parts of the patient undergoing the chemotherapeutic treatment.

In order for the optimum cooling temperature to be able to be set for each patient, the temperature control device can set the temperature control fluid with an accuracy of 1° C., but preferably with an accuracy of between 0.5° C. and 0.2° C. In order for the desired therapeutic effect to be achieved, it can be essential in the present context that the desired temperature, which is also referred to as the target temperature in the present description, is maintained as accurately as possible also during the cooling process.

In this application in connection with chemotherapy, the device is particularly advantageously equipped with a pressure device. Since the aim is to reduce the blood flow through the blood capillaries, it is of particular advantage here if the heat transfer unit is in uniform contact, i. e. as far as possible without any thermally insulating air pockets, with the skin regions of the selected region of the body of the patient. This is achieved by means of the pressure device.

For example, by means of time control of the device, the time which is required to reach the target temperature can be specified before the delivery of the chemotherapeutic agent is started.

However, temperature sensors on the heat transfer device can also be used instead to detect when the target temperature has been reached and then to output a corresponding signal.

Finally, a sensor for measuring blood flow can also be used here in a particularly advantageous manner. The cooling process is then started and continued until the blood flow has dropped to a predetermined value. By monitoring the patient's physiological values through the device, such as the heart rate and the blood pressure, it can be ensured at the same time that the cooling does not lead to an undesirable condition of the patient.

In one embodiment, the method is carried out at the same time as a chemotherapy treatment of the body of the human or animal, and is preferably started at least 20 minutes, preferably at least 30 minutes, before a start of the chemotherapy treatment, and/or is carried on until at least 20 minutes, preferably at least 30 minutes, preferably at least 40 minutes, preferably at least 1 hour, after an end of the chemotherapy treatment. This may provide good protection against certain side effects of chemotherapy treatment whilst not being overly time-consuming.

In one embodiment, the chemotherapy treatment is part of a sequence of chemotherapy treatments which are performed on the body of the human or animal, wherein the method is carried out at the same time as all chemotherapy treatments of said sequence of chemotherapy treatments. The inventor has found that the method in accordance with the invention produces best results (i.e. in terms of reducing or eliminating certain side effects of chemotherapy treatment) if it is carried out every time a chemotherapy treatment takes place. The start and finish time of the thermal treatment in relation to the start and finish time of the chemotherapy treatment (e.g. 30 minutes beforehand; 1 hour afterwards) may be kept the same for all chemotherapy treatments of the sequence of chemotherapy treatments, or may be varied.

In one embodiment, the method is carried out a number of times after a last chemotherapy treatment of said sequence of chemotherapy treatments, wherein said number is selected from the group consisting of 1, 2, 3 and 4. In this way, better protection from certain side effects of chemotherapy treatment can be provided than if no thermal treatment after the last chemotherapy treatment is carried out.

In one embodiment, the method is carried out a last time between 6 months and 18 months after the last chemotherapy treatment of said sequence of chemotherapy treatments. In this way, better protection from certain side effects of chemotherapy treatment can be provided than if the last thermal treatment is carried out at the same time as the last chemotherapy treatment, or only shortly afterwards (e.g. within one month).

In one embodiment, the chemotherapy treatment is part of a sequence of chemotherapy treatments which are performed on the body of the human or animal, wherein the method is carried out only once symptoms of chemotherapy-induced polyneuropathy (CIPN) or hand-foot syndrome (HFS) have been observed on the body of the human or animal. Since CIPN and HFS do not occur in every patient undergoing chemotherapy, it may in some cases be preferred to only carry out the thermal treatment if and when CIPN and HFS actually occur, although the results tend to be better (in terms of a long-term prevention of these symptoms) if the thermal treatment is performed as a prophylactic measure, as described above.

In one embodiment, the patient has breast or genital cancer.

In one embodiment, the patient is female.

In one embodiment, the chemotherapy is a Taxan-based chemotherapy regimen e.g., Paclitaxel, Nab-Paclitaxel, Docetaxel.

In one embodiment, the patient does not have one of the following diseases: Diabetes mellitus (of any type), neurological diseases that are involving peripheral nerve damage (e.g. Multiple Sclerosis, Amytrophic lateral sclerosis, Parkinson's disease), chronic pain syndrome, Cryoglobulinemia, cold hemagglutination, cold hives/cold contact hives, Raynaud's disease, significant peripheral artery disease.

In one embodiment, the chemotherapy treatment is part of a sequence of chemotherapy treatments which are performed on the body of the human or animal, wherein the method is carried out only once symptoms have been observed on the body of the human or animal which relate to a grade according to Common Terminology Criteria for Adverse Events (CTCAE) v5.0, wherein said grade is selected from the group consisting of:

Grade 1 or higher,
Grade 2 or higher,
Grade 3 or higher, and
Grade 4.

The grades according to Common Terminology Criteria for Adverse Events (CTCAE) v5.0 are explained further below.

In the examples mentioned above, it is assumed that the temperature control device heats or cools the selected region to a specific target temperature. However, instead of a constant target temperature, the temperature can also be changed during the treatment. This can be done by modulating the temperature/time curve. This modulation can preferably have a rectangular shape, a sinusoidal shape, a sawtooth shape or a trapezoidal shape in the temperature/time curve.

Further advantageous embodiments of the invention are explained in the following description in connection with the accompanying drawings. In the drawings.

Figure 1:
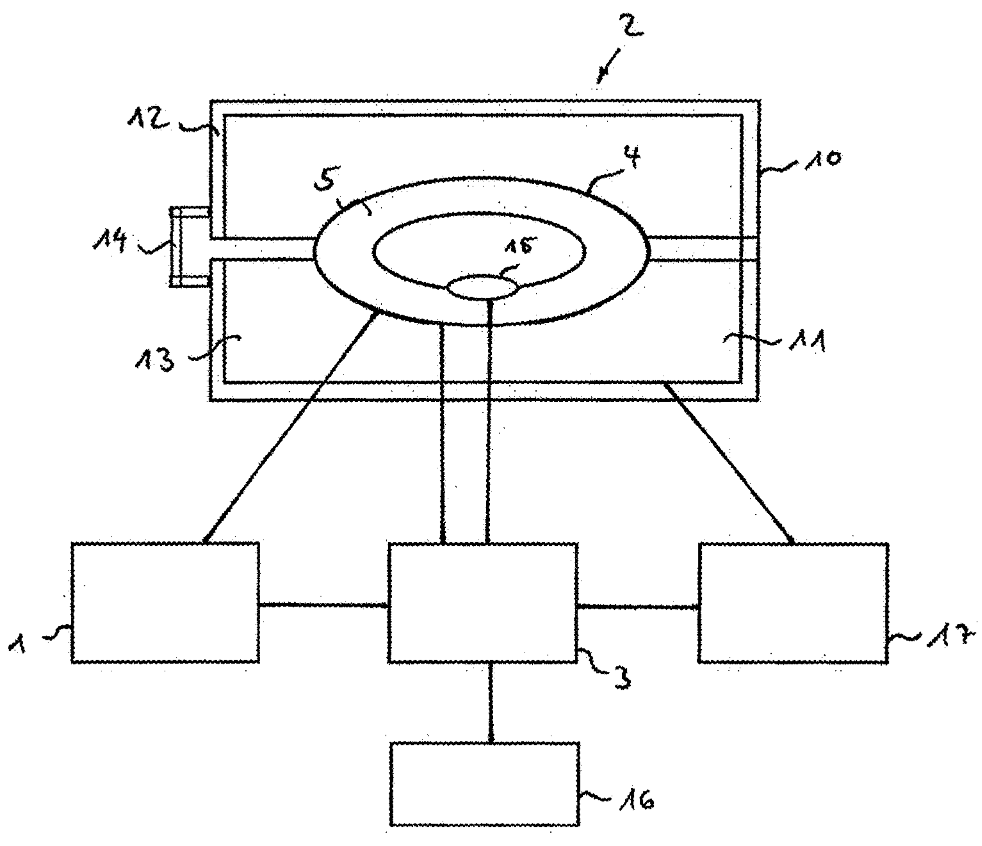
FIG. 1 shows a device in accordance with the invention for use in thermal therapy treatment.

FIG. 1 shows a device for use in the thermal therapy treatment of a selected region of the body of a human or of an animal, and in particular for use in the treatment of tissue damage after surgical interventions, of injuries, of inflammations and of chronic diseases of the rheumatic type, and in particular for the support of chemotherapeutic treatments, with a temperature control device 1, which is provided for tempering a temperature control fluid. The temperature control device 1 is connected, in a fluid conducting manner, to a heat transfer device 2, which is arranged for the transfer of heat to the selected region of the body, and which is further arranged to temper the heat transfer device 2 with a heat transferring temperature control fluid flowing through the heat transfer device 2. Furthermore, a control device 3 is connected to the temperature control device 1 and the heat transfer device 2, whereby the control device 3 is arranged to control the temperature control device 1 in order to cause the heat transfer device 2 to have at least partially an approximately uniform temperature in the region of a contact surface between the heat transfer device 2 and the selected region of the body to be tempered.

In this context, the heat transfer device 2 comprises at least one heat transfer unit 4, which is provided to be brought into contact with the selected region of the body, whereby the heat transfer unit 4 consists of a substantially flexible material, in which one or more temperature control fluid chambers 5 are arranged, through which the temperature control fluid can flow.

In this context, the heat transfer device further comprises a pressure device 10 which is adjacent to the heat transfer unit 4, wherein the pressure device 10 comprises at least one pressure unit 11 and a support device 12.

The pressure unit 11 is in communication with the support device 12, and the pressure unit 11 is provided in order to at least partially subject the heat transfer unit 4 to a pressure, which is then absorbed by the portion of the body to be treated as a contact pressure of the heat transfer device 2. For this purpose, the pressure unit 11 comprises at least one pressure chamber 13 with a predetermined or a variable internal pressure, and it is arranged to at least partially increase a contact pressure of the heat transfer device 2 on the selected region. In this context, the at least one pressure chamber 13 comprises a chamber which is filled with a pressure fluid, wherein the at least one chamber filled with a pressure fluid is formed by a flexible material. In this context, the pressure fluid in the at least one pressure chamber filled with a pressure fluid can be subjected to pressure via a pressure line which is connected to the at least one chamber filled with a pressure fluid, either manually via muscle power and/or with the help of a compressor 17, in order to change an internal pressure in the at least one chamber filled with a pressure fluid.

The support device 12 of the pressure device 10 further comprises a connecting device 14 which has at least one fixing element, and the connecting device 14 is constructed in such a way that it at least partially extends around the pressure device 10 and that it exerts supporting forces on the pressure device 10 in this surrounding position, which supporting forces at least partially contribute to fixing the pressure device 10 to the selected region of the body of a human or of an animal in a "deployed for use" condition.

Further, at least one sensor device 15 is provided, which is connected to the control device 3. The sensor device 15 is set up to measure a sensor signal between the selected region of the body and the skin contact surface. Here, the sensor signal can be present in optical, acoustic or digital form. In the example embodiment shown in FIG. 1, the sensor device 15 is mounted between the heat transfer unit 4 and the portion of the body to be treated, but other positions are also possible.

Further, at least one display device 16 is provided, wherein the display device 16 is connected to the control device 3 and is set up to output, to a user via the display device 16, the sensor signal which has been measured by the sensor device 15. The sensor signal can also be used for control with feedback, so that a region of a contact surface between the heat transfer device 2 and the portion of the body to be tempered has, at least in one region, an approximately uniform, preselected temperature.

Figure 2:
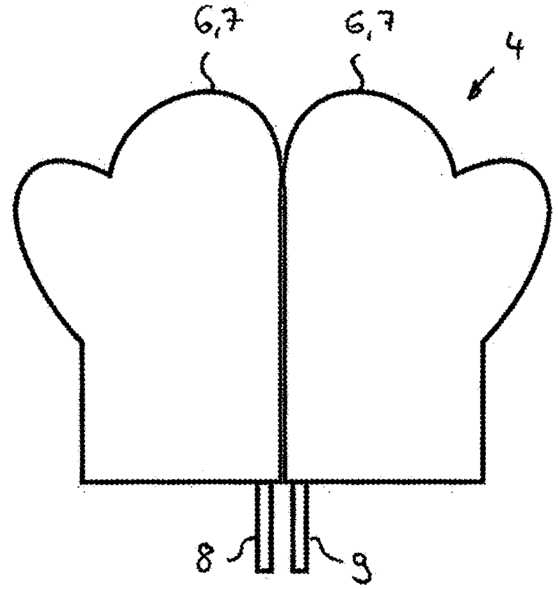
FIG. 2 shows a glove-shaped heat transfer unit in accordance with the invention in the unfolded state.

FIG. 2 shows a heat transfer unit 4 which is provided to be brought into contact with the selected region of the body, wherein the heat transfer unit 4 consists of a substantially flexible material in which one or more temperature control fluid chambers 5 (not shown) are arranged through which the temperature control fluid can flow.

In this context, the heat transfer unit 4 comprises:

at least a first flexible material layer 6 having at least a first skin contact surface which faces at least partially towards a selected region of the body of a human or of an animal, and having at least a first temperature control fluid contact surface which faces away from the first skin contact surface, at least a second flexible material layer 7 having at least a second temperature control fluid contact surface, which, between itself and the first temperature control fluid contact surface of the first flexible material layer 6, at least partially delimits one or more temperature control fluid chambers through which a heat transferring temperature control fluid can flow, wherein the heat transfer unit 4 further comprises:

at least a first connecting line 8 for supplying a heat transferring temperature control fluid to the heat transfer unit 4, at least a second connecting line 9 for discharging a heat transferring temperature control fluid from the heat transfer unit 4.

The use of flexible material layers 6, 7 is necessary because the region of the body to be tempered is not flat, but comprises concave and/or convex regions, and the flexibility of the material layers 6, 7 makes it possible to keep the distance between the heat transfer unit 4 and the region to be tempered as small as possible over the entire three-dimensional surface, whereby the heat transfer unit 4 preferably rests directly on the skin surface.

In this context, the heat transfer unit 4 has at least a first shape or can assume such a first shape in which it at least partially encloses the selected region of the body of a human or of an animal.

In a preferred variant, the heat transfer unit 4 has one of the following shapes, or can assume one of these shapes:

the shape of a cover enclosing the hand without subdivisions of the interior space;

the shape of a glove with partially separated covers for at least one finger, in particular the shape of a mitten with a partially separated cover for the thumb, as is shown in FIG. 2;

the shape of a finger glove with partially separated covers for each finger;

the shape of an at least partially fingerless glove, in which at least one finger is not enclosed.

However, the portion of the body to be treated can also be a foot or any other body part, in which case the heat transfer unit 2 has, or can assume, the shape of a shoe or stocking, or any other shape adapted to the respective body part.

Figure 3:
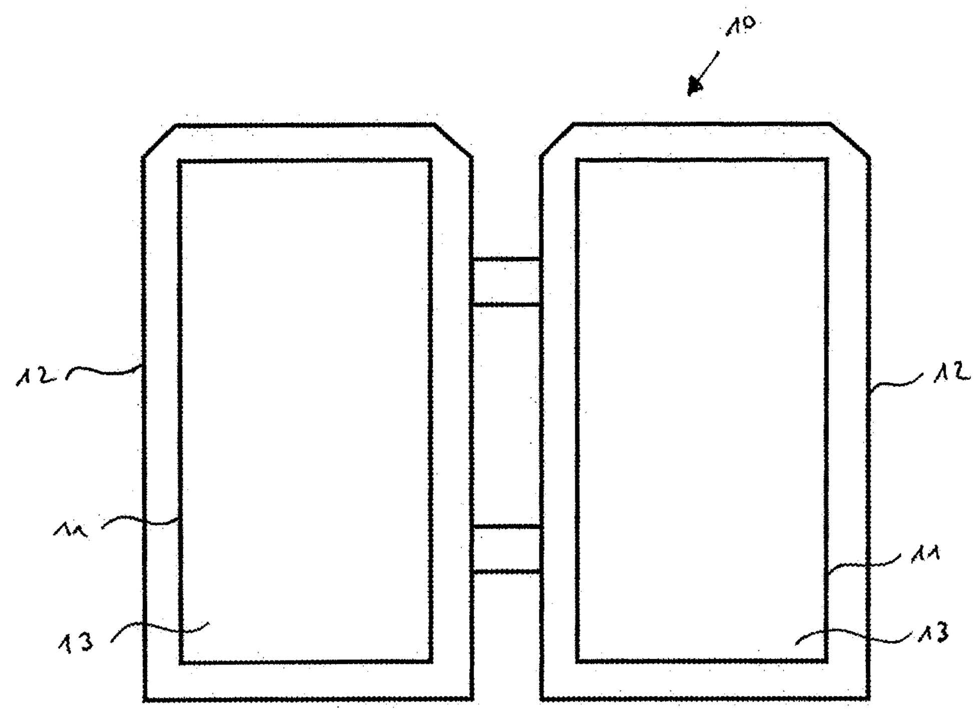
FIG. 3 shows a pressure device in accordance with the invention in the unfolded state.

FIG. 3 shows the pressure device 10, wherein the pressure device 10 comprises at least one pressure unit 11 and a support device 12, which is provided for building up a contact pressure. The pressure unit 11 is attached to the support device 12 and is provided for at least partially subjecting the heat transfer unit 4 to a pressure. For this purpose, the pressure unit 11 comprises at least one pressure chamber 13, which has a predetermined or a variable internal pressure and which is arranged to at least partially increase the contact pressure of the heat transfer device 2 on the selected region by means of the internal pressure. In this context, according to one embodiment, the pressure unit 11 may comprise a pressure chamber 13 in the form of a chamber which is filled with a pressure fluid, wherein the at least one chamber filled with a pressure fluid is delimited by a flexible material. In a further preferred embodiment, the at least one pressure unit 11 is made of an elastic material, such as preferably a type of foam rubber, a type of rubber, or a combination of these or similar materials, whereby the pressure unit 11 and the pressure chamber 13 are to be considered as the same component in this embodiment.

Figure 4:
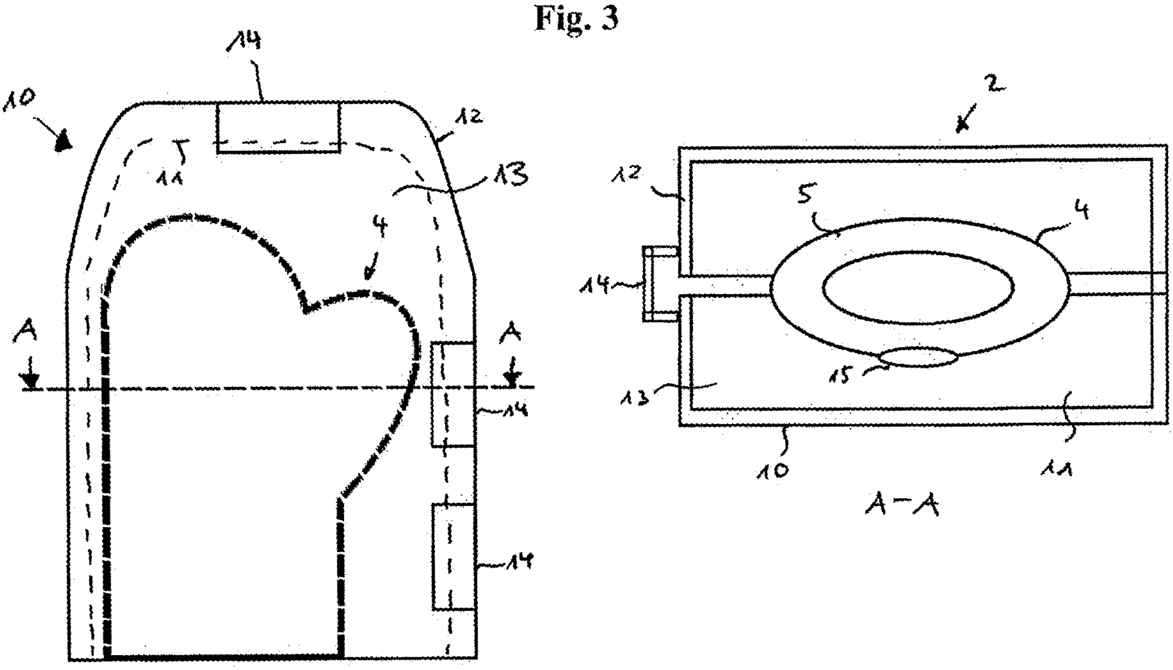
FIG. 4 shows a heat transfer unit in accordance with the invention in accordance with FIG. 1, in combination with a pressure device in accordance with the invention in accordance with FIG. 3.

FIG. 4 again shows the heat transfer device 2 from FIG. 1 and the pressure device 10 from FIG. 3 with slightly different dimensions. Here, the right-hand figure represents a section A-A through the section plane coming out of the plane of the drawing, along the dashed straight line A-A in the left-hand figure. In the left-hand figure, the heat transfer unit 4 of FIG. 2 is also indicated by dashed lines. Here, the heat transfer device 2 comprises at least one heat transfer unit 4, in which one or more temperature control fluid chambers 5 are arranged. A pressure device 10 is connected to the heat transfer unit 4, wherein the pressure device 10 comprises at least one pressure unit 11 and a support device 12. The support device 12 is attached to the pressure unit 11 and is provided so as to at least partially build up, via the heat transfer unit 4, a contact pressure of the heat transfer device 2 on the portion of the body to be treated. For this purpose, the pressure unit 11 comprises at least one pressure chamber 13. The pressure chamber 13 is arranged for at least partially increasing, by means of an internal pressure, the contact pressure of the heat transfer device 2 on the selected region. The pressure device 10 further comprises a support device 12, whereby the pressure device 10 is attached to the support device 12, and the pressure unit 11 is provided to at least partially subject the heat transfer unit 4 to a pressure. In this embodiment, the pressure device has three connecting devices 14, although preferably more, or fewer, connecting devices are conceivable. In this embodiment, each of the connecting devices 14 shown is of a one-piece construction; in a preferred embodiment, the connecting device is constructed in a circumferential manner, for example in the form of a zipper or a similar mechanism. In the embodiment shown in FIG. 4, the pressure unit 11 occupies a larger area, in a plan view, than the heat transfer unit 4, as well as being of one-piece construction, but, in relation to the heat transfer unit, smaller dimensions and multi-part pressure units are preferably also conceivable, which can be filled individually or jointly, through a common fluid connection, or can be controlled individually or jointly, with the help of a control device 3.

Figure 5:
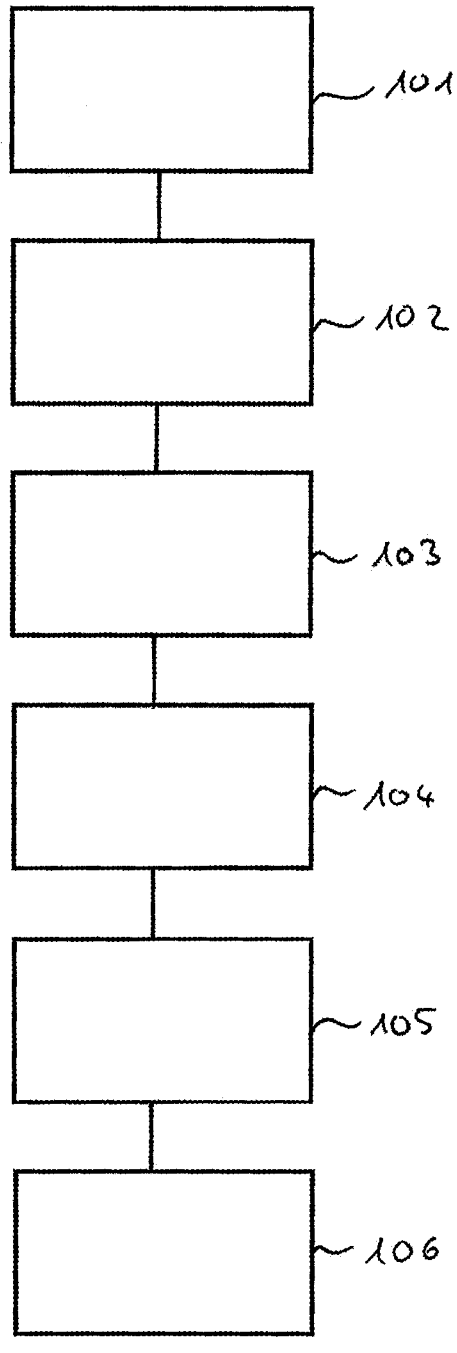
FIG. 5 shows a flow diagram of a method of operating the device in accordance with the invention.

FIG. 5 shows a flowchart of a method of operating a device for thermal therapy treatment of a selected region of the body of a human or of an animal in accordance with the invention. The method illustrated in FIG. 5 may use any of the devices previously described herein, it being appreciated that the invention is not limited solely to the use of such devices.

As shown in step 101 of FIG. 5, a heat transfer device 2 with a pressure device 10 is brought into contact with the selected region of the body in a "deployed for use" condition.

Step 102 illustrates applying, via the pressure device 10, a contact pressure acting on the selected region of the body.

Step 103 illustrates tempering, via a temperature control device 1 connected to the heat transfer device 2, the selected region of the body by causing a heat transferring heat control fluid to flow through a heat transfer unit 4 of the heat transfer device 2.

In this way, the region of a contact surface between the heat transfer device 2 and the portion of the body to be tempered has an approximately uniform temperature in at least one region.

In some embodiments, the selected region of the body may include, for example, hands and/or feet, as well as other regions of the body such as the arms, legs, chest, back, abdomen, and/or head. Additionally, the method may include fitting the thermal therapy device to uniformly contact a skin surface of the selected region, such as the hands and/or feet.

Further, in some embodiments, the pressure device 10 may be configured to generate or increase the contact pressure on the selected region of the body, for example, to improve thermal transfer to a skin surface of the selected region of the body.

Further, in some embodiments, the heat control fluid may be supplied to the heat transfer device 2 and may be maintained at a temperature of between about 15° C. and 17° C., or other suitable temperature, for the duration of the chemotherapy treatment, such that even tempering of the skin surface is achieved. In some embodiments, the heat control fluid may be water-based.

Further, in some embodiments, the temperature of the skin surface during the thermal therapy may be no more than 22° C., and in other embodiments, no more than 20° C.

In a preferred embodiment, the method of operating a device for thermal therapy treatment further comprises a step 104 of adjusting an internal pressure of a pressure unit 11 of the pressure device 10, wherein the pressure unit 11 comprises at least one chamber filled with a pressure fluid, wherein the internal pressure of the at least one chamber filled with a pressure fluid can be adjusted manually by means of muscle power of a user and/or by means of an external pressure source.

In a further preferred embodiment, the method of operating a device for thermal therapy treatment further comprises the step 105 of measuring a sensor signal by means of a sensor device 15 which is connected to the heat transfer device 2, and the step 106 of controlling, by means of a control device 3, the pressure device 10 which is connected to the control device 3, on the basis of the measured sensor signal.

In this context, the control device 3 is preferably set up in such a way that, together with the heat transfer device 2 and the temperature control device 1, it forms a control loop using the sensor signal measured by the sensor device 15, so that an approximately uniform, preselected temperature is feedback controlled in at least one region in the region of a contact surface between the heat transfer device and the portion of the body to be tempered. In this context, by avoiding thermally insulating air pockets between the heat transfer unit and the region of the body to be tempered, the heat transfer is significantly improved.

CLINICAL STUDY RESULTS/EXAMPLES

A number of studies have been carried out by, or on behalf of, the present applicant, details of which are given below. All of the studies were carried out in a confidential setting. The ambient temperature was at room temperature (about 22° C.).

Example 1

A device (a temperature control device, a heat transfer unit generally in the form of a hand cuff, as well as connecting hoses) in accordance with an embodiment of the present invention was used to cool a human hand. A temperature sensor was attached to the hand using several layers of adhesive tape. This way of attaching the temperature sensor to the hand was chosen so as to ensure, as far as reasonably possible, that the sensor measures the temperature of the skin of the hand rather than a temperature prevailing within a space between the skin and the hand cuff.

First, the skin temperature at different locations of the hand was measured without any cooling and without the hand being inserted in the hand cuff. The average temperature was about 29° C., with slight variations depending on the location on the hand (palm of the hand, back of the hand, or between fingers). All measurements were between 27° C. and 30° C.

Next, the hand was inserted in the hand cuff. Cooling fluid, in this case water, was cooled by the temperature control device and circulated between the temperature control device and the hand cuff. The target temperature of the cooling fluid was set to 10° C. on the temperature control device. The temperature control device kept the temperature of the cooling fluid stable at about 10° C.±0.5° C. (within the temperature control device). Due to thermal losses between the temperature control device and the hand cuff, the average temperature of the cooling fluid arriving at the hand cuff was about 11° C. Initially, no pressure (using a pressure device, as described above) was applied to generate an (additional) contact pressure between the hand cuff and the hand. After about 7 minutes, the hand temperature had gradually dropped to about 25° C. and remained approximately stable at that temperature.

Pressure was then applied by the pressure device so as to increase the contact pressure and to achieve a better (thermal) contact between the hand cuff and the hand. As a result, the temperature of the hand dropped more steeply than when the hand was first placed in the hand cuff without additional pressure. About 7 minutes after the beginning of the application of pressure, the hand temperature had gradually dropped to about 18° C. Eventually, the hand temperature settled at about 15° C. This was achieved approximately 18 minutes after the beginning of the application of pressure.

The pressure (as generated by the pressure device) was then removed but the hand cuff remained in place, and cooling fluid continued to be circulated. The hand temperature slowly increased again, by about 1° C. over the course of about 6 minutes. Once the hand cuff was removed completely, the temperature of the cooled hand increased only slowly, by about a further 3° to an average of about 19° (between 17° and 21°, depending on the location on the hand) over the course of a further 8 minutes.

Example 1 shows (inter alia) the following results:

a) The target temperature set on the temperature control device can differ significantly from the actual temperature measured at the skin temperature, in particular dependent on the contact pressure.

b) Even without the application of (additional) pressure, a reasonable degree of cooling can be achieved. A higher degree of cooling can be achieved through the application of (additional) pressure.

c) As the therapeutic effect is dependent on the temperature of the tissue to be cooled, certain embodiments of the present invention seek to ensure that the skin is actually cooled down to a target skin temperature. This produces better results than a therapy which merely ensures that the temperature of the cooling fluid (while still in the temperature control device) is cooled to a particular temperature whilst ignoring the actual skin temperature. The same applies if the therapy seeks to heat the tissue.

Example 2

The setup and the principle of the experiment in Example 2 corresponded in essence to that of Example 1, except that the experiment was carried out on a human foot instead of a human hand.

A device (a temperature control device, a heat transfer unit generally in the form of a slipper, as well as connecting hoses) in accordance with an embodiment of the present invention was used to cool a human foot. A temperature sensor was attached to the foot using several layers of adhesive tape. This way of attaching the temperature sensor to the foot was chosen so as to ensure, as far as reasonably possible, that the sensor measures the temperature of the skin of the foot rather than a temperature prevailing within a space between the skin and the slipper.

First, the skin temperature at different locations of the foot was measured without any cooling and without the foot being inserted in the slipper. The average temperature was about 31° C., with slight variations depending on the location on the foot (sole of the foot, back of the foot or between toes, here between the big toe and the second toe). All measurements were between 30° C. and 32° C.

Next, the foot was inserted in the slipper. Cooling fluid, in this case water, was cooled by the temperature control device and circulated between the temperature control device and the slipper. The target temperature of the cooling fluid was set to 10° C. on the temperature control device. The temperature control device kept the temperature of the cooling fluid stable at about 10° C.±0.5° C. (within the temperature control device). Due to thermal losses between the temperature control device and the slipper, the average temperature of the cooling fluid arriving at the slipper was about 11° C. Initially, no pressure (using a pressure device, as described above) was applied to generate an (additional) contact pressure between the slipper and the foot. After about 7 minutes, the foot temperature had gradually dropped to about 27° C. and remained approximately stable at that temperature.

Pressure was then applied by the pressure device so as to increase the contact pressure and to achieve a better (thermal) contact between the slipper and the foot. As a result, the temperature of the foot dropped. Depending on the location on the foot, this drop was slightly steeper than when the foot was first placed in the slipper without additional pressure. Between about 7 and 20 minutes (depending on the location on the foot) after the beginning of the application of pressure, the foot temperature had gradually dropped to about 22° C. Eventually, the foot temperature settled at about 17° C. (with some variation, depending on the location on the foot). This was achieved approximately 40 to 45 minutes after the beginning of the application of pressure.

The pressure (as generated by the pressure device) was then removed but the slipper remained in place, and cooling fluid continued to be circulated. The foot temperature slowly increased again, by about 1° C. over the course of about 6 minutes. Once the slipper was removed completely, the temperature of the cooled foot increased only slowly, by about a further 2° to an average of about 19° (between 17° and 20.5°, depending on the location on the foot) over the course of a further 8 minutes.

Example 2 shows similar results as Example 1, albeit with somewhat different rates of cooling and slightly different amounts of temperature variation depending on the location on the foot/hand.

Example 3

This clinical trial concerned 130 female patients with breast cancer, who underwent a taxane-based chemotherapy, in particular using Paclitaxel or Docetaxel. Before, during and after each chemotherapy treatment, their hands and feet were continuously cooled to about 10 to 12° C. (skin temperature) using a method/device according to an embodiment of the present invention. Cooling started 30 minutes before the chemotherapy treatment and continued for 30 to 60 minutes after the end of each chemotherapy treatment.

The occurrence of side-effects (adverse events, "AE") resulting from the chemotherapy was then recorded using the "Common Terminology Criteria for Adverse Events (CTCAE) v5.0". This uses clinical descriptions to define five grades depending on the severity of adverse events, plus a "Grade 0", as follows:

Grade 0 No AE observed.

Grade 1 Mild; asymptomatic or mild symptoms; clinical or diagnostic observations only; intervention not indicated.

Grade 2 Moderate; minimal, local or noninvasive intervention indicated; limiting age-appropriate instrumental ADL (Activities of Daily Living). Instrumental ADL refers to preparing meals, shopping for groceries or clothes, using the telephone, managing money, etc.

Grade 3 Severe or medically significant but not immediately life-threatening; hospitalization or prolongation of hospitalization indicated; disabling; limiting self care ADL. Self care ADL refers to bathing, dressing and undressing, feeding self, using the toilet, taking medications, and not bedridden.

Grade 4 Life-threatening consequences; urgent intervention indicated.

Grade 5 Death related to AE.

In this clinical trial, examples of Grade 2 AE were tingling, moderate numbness, reddening of the skin or other painful sensations. Examples of Grade 3 AE were extensive numbness, reduced ability of using arms and legs, the formation of blisters, skin flakes, bleeding of the skin, ulcerations or detachment of one or more fingernail or toenail, as well as strong pain.

In this clinical trial, the highest grade of AE reported during the entire course of the chemotherapy was:

Grade 0: 51 patients

Grade 1: 70 patients

Grade 3: 1 patient

Grade 4: 0 patients

Grade 5: 0 patients

In other words, using a method/device in accordance with an embodiment of the present invention, 93% of the patients (n=121) had no symptoms or only non-limiting symptoms (Grades 0 and 1), 6.2% (n=8) had Grade 2 symptoms and less than 1% (n=1) had Grade 3 symptoms. None of the patients had Grade 4 or 5 symptoms.

By way of contrast, in studies (involving a large number of patients) reported in scientific journals without the use of a method/device in accordance with an embodiment of the present invention, CIPN was reported in 60% of all patients, with one study reporting 4.1% and another study reporting 6-20% of patients with Grade 3 or 4 symptoms. Other studies reported that 50% of patients undergoing taxane-based chemotherapy (without the use of a method/device in accordance with an embodiment of the present invention) showed Grade 2 or 3 symptoms.

A comparison between, on the one hand, the clinical trial using a method/device in accordance with an embodiment of the present invention, and on the other hand, the studies reported in scientific journals, demonstrates that the methods/devices in accordance with the present invention significantly reduce the prevalence of AE from chemotherapy, and in particular the prevalence of AE in higher grades according to CTCAE v5.0.

Example 4

This clinical trial was based on the clinical trial of Example 3, i.e. the clinical trial of example 3 was followed by further treatments using a method/device in accordance with an embodiment of the present invention at four different points in time after the last chemotherapy treatment. These four points in time were chosen to be: 4 weeks, 4 months, 7 months and 10 months after the last chemotherapy treatment.

Whilst at the end of the chemotherapy treatment, 93% of the patients had no symptoms or only non-limiting symptoms (see example 3), this percentage increased to 98% at 10 months after the last chemotherapy treatment.

Example 5

This clinical trial was similar to the clinical trial of Example 3. This clinical trial concerned 38 female patients with breast cancer, who underwent a taxane-based chemotherapy, in particular using Paclitaxel or Docetaxel. However, initially they did not use a method/device in accordance with an embodiment of the present invention when they started their chemotherapy, and only did so once they developed symptoms of CIPN and/or HFS. They then carried on using the method/device in accordance with an embodiment of the present invention for all subsequent chemotherapy treatments and until 4 weeks after the last such treatment.

The prevalence of the symptoms according to CTCAE v5.0 was recorded at the time of the last chemotherapy treatment, and four weeks thereafter, i.e. the percentage of patients having symptoms of Grade 0, 1, 2 etc. In addition, the highest grade encountered during the period of observation was recorded. This produced the following results:

| | Grade 0 | Grade 1 | Grade 2 | Grade 3 |
|---|---|---|---|---|
| Highest Grade | 0% | 50% | 45% | 5% |
| Grade at last therapy | 16% | 59% | 22% | 3% |
| Grade at 4 weeks after last therapy | 31% | 50% | 17% | 2% |

The above results demonstrate a clear shift from symptoms in Grades 2 and 3 towards symptoms in Grade 0 (i.e. no symptoms) or in Grade 1 (non-limiting symptoms) during the time when a method/device in accordance with an embodiment of the present invention was used.

Example 6

The clinical trial of Example 5 was continued, i.e. a therapy in accordance with an embodiment of the present invention was provided at 4, 7, 10 and 14 months after the last chemotherapy treatment. The trend towards Grade 0 (no symptoms) or Grade 1 (non-limiting symptoms) continued during this additional period of observation.

Example 7

Further clinical trials similar to those of Examples 3 to 6 were carried out with patients undergoing chemotherapy to treat a variety of types of cancer, including breast, gynecological, and pancreatic cancer, and using a variety of chemotherapeutic agents such as those listed above. The results in terms of AE, in particular the shift towards lower grades (according to CTCAE v5.0) as a result of the treatment in accordance with an embodiment of the present invention), were generally similar to those of Examples 3 to 6.

Example 8

The setup and the principle of the experiment in Example 8 corresponded in essence to that of Examples 1 and 2. However, the temperature control device was set to a higher target temperature of between about 15° C. and 17° C. (instead of about 10° C.). It has been found that a skin temperature (hands and feet) of between about 20° C. and 22° C. is sufficient to significantly reduce the likelihood of negative (chemotherapy-related) effects developing (such as CIPN, for example). Using the higher target temperature of about 15° C. and 17° C. (as set on the temperature control device) was found to be sufficient to result in skin temperatures of between about 20° C. and 22° C. Subjects participating in this experiment reported that cooling the skin to about 20° C. and 22° C. (using a target temperature of about 15° C. and 17° C. as set on the temperature control device) feels more pleasant than cooling the skin to the somewhat lower temperature range used in Examples 1 and 2 (target skin temperature of about 15° C. and 17° C., using a target temperature of about 10° C. as set on the temperature control device).

Example 9

The following study is being conducted:

In this trial, patients receiving Taxan-based chemotherapy regimen e.g. paclitaxel, nab-paclitaxel or docetaxel in gynecological malignancies such as ovarian cancer, breast cancer, endometrial cancer or cervical cancer will either receive cooling of hands and feet during the application of above-mentioned substances or not. The cooling will be provided by a machine called Hilotherm ChemoCare unit and will be administered constantly at a temperature of 15-17° C. Randomization will be 50:50.

if a patient is randomized in the non-interventional arm, no cooling is allowed during the application of the chemotherapy.

To assess the occurance and the extent of peripheral neuropathy, a neurological examination will take place before the start of chemotherapy, in the middle of the planned cycles of chemotherapy and after the completion of the regimen.

Quality of life and the subjective impacts of peripheral neuropathy will be evaluated via questionnaires.

Inclusion Criteria:

- Written consent for participation in this trail
- Age ≥18 years
- Female
- Breast or genital cancer of the woman
- Planned application of a Taxan-based chemotherapy regimen (Paclitaxel, Nab-Paclitaxel, Docetaxel) independent of the therapy line
- Taxan- and Platin-naivity
- Sufficient knowledge of the German language to assure an adequat survey of patient's history Exclusion Criteria:

- pre-existing peripheral polyneuropathy
- chemotherapy with taxan- and/or carboplatin-based regimens in a preceding therapy
- Existence of one of the following diseases: Diabetes mellitus (of any type), neurological diseases that are involving peripheral nerve damage (e.g. Multiple Sclerosis, Amytrophic lateral sclerosis, Parkinson's disease), chronic pain syndrome, Cryoglobulinemia, cold hemagglutination, cold hives/cold contact hives, Raynaud's disease, significant peripheral artery disease,
- Lack of knowledge of German
- Males Primary Outcome measures:

| Outcome Measure | Measure Description | Time Frame |
|---|---|---|
| incidence of peripheral polyneuropathy | The primary endpoint of this study is the comparison of the incidence of a peripheral polyneuropathy (clinical Total Neuropathy Score cTNS ≥ 11) in patients with gynecologic malignoma that are undergoing Taxan-based chemotherapy regimen with or without a preventive hilotherapy of hands and feet. | Up to one year after the end of chemotherapy. |

Secondary Outcome measures:

| Outcome Measure | Measure Description | Time Frame |
|---|---|---|
| Changes in the result of electrophysical examinations | Changes in the result of electrophysical examinations before and after chemotherapy. | From the beginning to the end of chemotherapy, exact time frame depending on the chemotherapy regimen, assessed up to 30 weeks. |
| Adverse effects of hilotherapy | Adverse effects of hilotherapy documented as any adverse event. | Up to one year after the end of chemotherapy. |
| Tolerance of chemotherapy | Tolerance of chemotherapy measured as the proportion of patient with dose reduction or | From the beginning to the end of chemotherapy, exact time frame |

-continued

| Outcome Measure | Measure Description | Time Frame |
|---|---|---|
| | premature end of chemotherapy. | depending on the chemotherapy regimen, assessed up to 30 weeks. |
| Patient reported Quality of Life | Quality of Life of patients measured with the EORTC QLQ-C30 questionnaire | Up to one year after the end of chemotherapy. |
| Residual Symptoms of Chemotherapy-induced polyneuropathy | Comparison of the time of regression, cTNS score of persisting symptoms and amount of patients without residues after end of chemotherapy and follow-up between patients with and without preventive hilotherapy. | Up to one year after the end of chemotherapy. |
| Subjective extent of CIPN | Subjective extent of CIPN as measured with the EORTC QLQ-CIPN20 (quality of life questionnaire regarding chemotherapy-induced peripheral neuropathy with 20 questins) questionnaire. The qustionnaire consits of 20 items on 3 scales. The minimum is 0, the maximum is 100 points. The higher the score, the worse the CIPN. | Up to one year after the end of chemotherapy. |
| Acceptance of hilotherapy | Acceptance of hilotherapy measured as the amount of patients that have to stop local cold application during a session (up to 5 minutes) or terminate earlier or stop the treament completely for the rest of chemotherapy. | From the beginning to the end of chemotherapy, exact time frame depending on the chemotherapy regimen, assessed up to 30 weeks. |

The device is operated as follows:

Preparation

1. Check the device for visible damage and ensure it's clean.

Place the device on a stable, flat surface near the patient.

Ensure cuffs (hand and foot) are available and clean.

2. Filling the Water Tank

Open the water tank compartment.

Fill with distilled water up to the indicated level.

Close the compartment securely.

3. Powering On

Connect the device to a power source.

Press the power button to switch on.

Wait for the system to initialize.

4. Setting the Temperature

Use the menu navigation buttons to access the temperature settings.

Set the desired temperature (typically 15-17° C. for CIPN prevention).

Confirm the setting.

5. Connecting the Cuffs

Attach the hand and foot cuffs to the designated ports on the device.

Ensure connections are secure to prevent leaks.

Position the cuffs on the patient's hands and feet.

6. Starting the Therapy

Press the start button to begin cooling.

Monitor the display to ensure the temperature remains stable.

Therapy duration typically matches the chemotherapy infusion time.

7. Ending the Session

Press the stop button to end the cooling session.

Carefully remove the cuffs from the patient.

Disconnect the cuffs from the device.

8. Post-Use Maintenance

Empty and clean the water tank if needed.

Disinfect cuffs according to hygiene guidelines.

Store the device and accessories in a clean, dry place.

Further Findings

Common to all of the above examples was that the vast majority of patients (about 75%) felt that the cold applied by the device in accordance with an embodiment of the present invention did not result in any particular discomfort. 89 patients were asked "how did you feel about the cold?"; their answers were:

Very comfortable: 33 patients

A bit cold: 33 patients

Cold: 14 patients

Very cold: 7 patients

Too cold: 2 patients

This contrasts with previous treatments in which ice packs, ice buckets or similar were used to cool hands and/or feet, which is considered to be very uncomfortable by patients. In addition, and perhaps more importantly, such treatments often resulted in skin and tissue damage (frost burn/paralysis) and reactive hyperemia, whereas these side effects did not occur in the clinical trials in which a method/device in accordance with an embodiment of the present invention was used.

Further, the use of a method/device in accordance with an embodiment of the present invention did not appear to affect the efficacy of the chemotherapy treatment.

LIST OF REFERENCE SIGNS

1 temperature control device

2 heat transfer device

3 control device
4 heat transfer unit
5 temperature control fluid chamber
6 first flexible material layer
7 second flexible material layer
8 first connecting line
9 second connecting line
10 pressure device
11 pressure unit
12 support device
13 pressure chamber
14 connecting device
15 sensor device
16 display device
17 compressor
101 bringing into contact
102 applying
103 tempering
104 adjusting
105 measuring
106 controlling

The invention claimed is:

1. A method of treating or preventing chemotherapy induced polyneuropathy (CIPN) in a patient receiving chemotherapy treatment, the method comprising:

providing thermal therapy to a selected region of a body of the patient, the selected region comprising a hand or a foot, wherein the thermal therapy comprises:

fitting a thermal therapy device to uniformly contact a skin surface of the selected region of the body having convex and concave regions, wherein the thermal therapy device comprises a flexible material having a skin contact surface facing towards the selected region, wherein the flexible material is fitted to the selected region of the body such that the skin contact surface conforms to the convex and concave regions of the selected region of the body in a manner such that air pockets between the skin contact surface and the skin surface are avoided; and providing a temperature control device to supply the thermal therapy device with a temperature control fluid;

maintaining a temperature of the temperature control fluid to be within the range of between about 15° C. and 17° C. for the duration of the chemotherapy treatment, such that even tempering of the skin surface is achieved and a temperature of the skin surface of the selected region of the body remains within a range of about 15° C. to about 22° C.;

thereby reducing metabolism and blood flow in the selected region such that less chemotherapy drug reaches the blood capillaries of the selected region.

2. The method according to claim 1, wherein the temperature of the skin surface during the thermal therapy is no more than 20° C.

3. The method according to claim 1, wherein the thermal therapy is provided for at least 20 minutes after starting the chemotherapy treatment.

4. The method according to claim 1, wherein the temperature control fluid is water-based.

5. The method of claim 1, wherein the chemotherapy treatment is part of a sequence of chemotherapy treatments, and the thermal therapy is carried out at the same time as each chemotherapy treatment of said sequence.

6. The method of claim 1, wherein the thermal therapy is commenced at least 30 minutes before a start of the chemotherapy treatment.

7. The method of claim 1, wherein the thermal therapy is maintained throughout the entire administration of the chemotherapeutic agent.

8. A method of treating or preventing chemotherapy induced polyneuropathy (CIPN) in a patient receiving chemotherapy treatment, the method comprising:

providing thermal therapy to a selected region of a body of the patient, the thermal therapy being delivered using a thermal therapy device, the thermal therapy device comprising:

a heat transfer unit provided to be brought into contact with the selected region of the body, the heat transfer unit being configured to receive a temperature control fluid;

a pressure device configured to generate, or to increase, a contact pressure of the heat transfer unit on the selected region of the body, to improve thermal transfer between the heat transfer unit and the selected region of the body; and a temperature control device provided to control a temperature of the temperature control fluid; and cooling the selected region of the body to a target skin temperature, using a temperature control fluid that is no more than 7° C. cooler than the target skin temperature, such that even tempering of the skin surface is achieved;

thereby reducing metabolism and blood flow in the selected region such that less chemotherapy drug reaches the blood capillaries of the selected region.

9. The method of claim 8, wherein the thermal therapy comprises cooling the selected region of the body to a target skin temperature, using a temperature control fluid that is no more than 5° C. cooler than the target skin temperature.

10. The method of claim 8, wherein the temperature control fluid is between about 15° C. and 17° C.

11. The method according to claim 8, wherein the selected region of the body comprises a hand.

12. The method according to claim 8, wherein the selected region of the body comprises a foot.

13. The method according to claim 8, wherein the temperature control fluid is water-based.

14. A method of increasing adherence to chemotherapy treatment, the method comprising:

administering chemotherapy to a patient in need thereof; and providing thermal therapy to a selected region of a body of the patient to prevent CIPN thereby increasing treatment adherence, wherein the thermal therapy comprises fitting a thermal therapy device to uniformly contact a skin surface of the selected region of the body having convex and concave regions, wherein the thermal therapy device comprises a flexible material having a skin contact surface facing towards the selected region, wherein the flexible material is fitted to the selected region of the body such that the skin contact surface conforms to the convex and concave regions of the selected region of the body in a manner such that air pockets between the skin contact surface and the skin surface are avoided, wherein the selected region comprises a hand or a foot;

providing a temperature control device to supply the thermal therapy device with the temperature control fluid; and maintaining a temperature of a temperature control fluid to be within the range of between about 15° C. and 17° C. for the duration of the chemotherapy treatment, such that even tempering of the skin surface is achieved and a temperature of the skin surface of the selected region of the body remains within a range of about 15° C. to about 22° C.;

thereby reducing metabolism and blood flow in the selected region such that less chemotherapy drug reaches the blood capillaries of the selected region.

15. The method according to claim 14, wherein the temperature of the skin surface during the thermal therapy is no more than 20° C.

16. The method according to claim 14, wherein the temperature control fluid is water-based.

* * * * *